US007008614B2

(12) United States Patent
Kitaguchi et al.

(10) Patent No.: US 7,008,614 B2
(45) Date of Patent: Mar. 7, 2006

(54) LIPOSOME CONTAINING HYDROPHOBIC IODINE COMPOUND AND X-RAY CONTRAST MEDIUM FOR RADIOGRAPH COMPRISING THE LIPOSOME

(75) Inventors: Hiroshi Kitaguchi, Kanagawa (JP); Kazuhiro Aikawa, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 519 days.

(21) Appl. No.: 10/223,461

(22) Filed: Aug. 20, 2002

(65) Prior Publication Data

US 2003/0086875 A1 May 8, 2003

(30) Foreign Application Priority Data

Aug. 20, 2001 (JP) .............................. 2001-249305
Aug. 20, 2001 (JP) .............................. 2001-249306

(51) Int. Cl.
*A61K 49/00* (2006.01)
*A61K 9/127* (2006.01)
(52) U.S. Cl. ..................... 424/9.45; 424/450
(58) Field of Classification Search ................ 424/9.4, 424/9.44, 9.454, 9.455, 450, 9.45, 9.451, 424/9.452, 9.453
See application file for complete search history.

(56) References Cited

U.S. PATENT DOCUMENTS 5,550,263 A * 8/1996 Hersl of et al. ............... 554/78
5,676,928 A * 10/1997 Klaveness et al. ........ 424/9.321

FOREIGN PATENT DOCUMENTS

| GB | 2 157 283 A | 10/1985 |
| WO | WO 92/21384 A1 | 12/1992 |
| WO | WO 01/82977 A1 | 11/2001 |

OTHER PUBLICATIONS

Radiolabeled Cholesteryl Iopanoate\Acetylated Low Density Lipoprotein as a Potential Probe for Visualization of Early Atherosclerotic Lesions in Rabbits Pharmaceutical Research, vol. 16, No. 3 1999 p. 420-426.
XP-009003943—R .E. Counsell et al., Potential Organ- or Tumor-Imaging Agents. 21. Acyl-Labeled Esters of Cholesterol, J. Med. Chem. (1981), vol. 24, No. 1, pp. 5-6.
XP-009003944—R. H. Seevers et al.. Potential Organ- or Tumor-Imaging Agents. 22. Acyl-Labeled Cholesterol Esters, J. Med. Chem. (1982), vol. 25, No. 6, pp. 618-621.
XP-000985456—R. E. Counsell et al., Potential Tumor- or Organ-Imaging Agents XXIV: Chylomicron Remnants as Carriers for Hepatographic Agents, Journal of Pharmaceutical Sciences (1983), vol. 72, No. 8, pp. 898-901.
XP-002942252—W. Xiao et al., Radiolabeled Cholesteryl Iopanoate/Acetylated Low Density Lipoprotein as a Potential Probe for Visualization of Early Atherosclerotic Lesions in Rabbits, Pharmaceutical Research, NY (1999), vol. 16, No. 3, pp. 420-426.
XP-002228681—Douglas . A. Bakan et al., Physicochemical Characterization of a Synthetic Lipid Emulsion for Hepatocyte-Selective Delivery of Lipophilic Compounds: Application to Polyiodinated Triglycerides as Contrast Agents for Computed Tomography, Journal of Pharmaceutical Sciences, vol. 85, No. 9 (1996), pp. 908-914.
Marc A. Longino et al., Formulation of Polyiodinated Triglyceride Analogues in a Chylomicron Remnant-Like Liver-Selective Delivery Vehicle, Pharmaceutical Research, vol. 13, No. 6 (1996), pp. 875-879.

* cited by examiner

*Primary Examiner*—Michael Hartley
(74) *Attorney, Agent, or Firm*—Sughrue Mion, PLLC

(57) ABSTRACT

A liposome containing a hydrophobic iodine compound represented by the following general formula (I) as a membrane component:

$$R^1{-}CO_2{-}R^2$$

wherein $R^1$ represents a substituted or unsubstituted 2,3,5-triiodophenyl group or a substituted or unsubstituted 3,4,5-triiodophenyl group; and $R^2$ represents a hydrocarbon group having 10 or more carbon atoms, and an X-ray contrast medium, which comprises said liposome which is used for radiography of a vascular disease.

11 Claims, 3 Drawing Sheets

LIPOSOME CONTAINING HYDROPHOBIC IODINE COMPOUND AND X-RAY CONTRAST MEDIUM FOR RADIOGRAPH COMPRISING THE LIPOSOME

FIELD OF THE INVENTION

The present invention relates to a liposome. More specifically, the invention relates to a liposome that contains a particular class of hydrophobic iodine compound and can be utilized for a method for imaging a lesion in contrast to non-pathological site by selectively accumulating the hydrophobic iodine compound in the lesion. The present invention also relates to an X-ray contrast medium which selectively accumulates in a tissue or lesion, in which macrophages localize, and enables imaging thereof in contrast to the other sites.

RELATED ART

In the modern society, especially in the societies of advanced countries, opportunities of ingesting high calorie and high fat diet are increasing. For this reason, mortalities due to ischemic diseases resulting from arteriosclerosis (heart diseases such as myocardial infarction and angina pectoris, cerebrovascular diseases such as cerebral infarction and cerebral hemorrhage) have been increasing. Therefore, it has been desired to diagnose such conditions at an early stage to employ an appropriate treatment. However, no satisfactory method is available for diagnosing progress of arteriosclerosis at an early stage before the onsets of the aforementioned diseases.

Methods for diagnosing arteriosclerosis are basically classified into non-invasive methods and invasive methods in which a catheter or the like is inserted into an artery. Among them, typical non-invasive methods include X-ray angiography and ultrasonography. However, by these methods, it is almost impossible to detect arteriosclerosis at an early stage, especially constriction of coronary artery, that causes myocardial infarction or angina pectoris, at an early stage before the onset of these diseases.

CT. MRI and the like may sometimes be used as another class of non-invasive methods. However, these methods have been mainly developed for detection of tumors, and accordingly, they have a problem of a low resolution of arteriosclerotic lesions. In addition, the methods require expensive and large-scale apparatuses, which limits employable hospitals and general applicability.

As the invasive methods, intravascular echo, vascular endoscope and the like have been used. It is recognized that an arteriosclerotic lesion with a thickness as thin as 0.1 mm can be measured by these methods. However, for employment of these methods, it is necessary to arterially insert an ultrasonic oscillator or an endoscope attached to an end of a catheter, which may result in serious physical stress and heaviness as well as a risk of a patient. Therefore, although these methods have been used therapeutically for patients after the attack of myocardial infarction and the like or as secondary prophylaxis, they cannot be used for a diagnostic purpose to know as to presence or absence or a degree of progress of arteriosclerosis in a patient before onset.

Among the aforementioned methods, a method most widely used for identification of a lesion of arterial vasoconstriction is X-ray angiography. This method comprises the step of administration of a water-soluble iodine contrast medium to visualize vascular flows, and detecting a lesion at which the flows are obstructed. Most of X-ray contrast mediums practically used are compounds with a triiodophenyl group which are made water-soluble. These mediums are used for diagnoses of lumen shapes, presence of constriction and the like by administration into lumens such as blood vessel, urinary duct, and oviduct. However, these compounds are rapidly excreted from such lumens without interaction with a tissue or a lesion, and therefore, they are not useful for diagnosing a tissue or a lesion in more detail. Moreover, these methods can only detect a lesion where constriction progresses 50% or more and fail to detect a lesion before the onset of attack of an ischemic disease. Therefore, an X-ray contrast medium has been desired that selectively accumulates in a target tissue or a lesion to provide an image with clear contrast to the other sites.

For example, J. Pharm. Sci., 72 (8), 898 (1983); Invest. Radiol., 18 (3), 275 (1983); Steroids, 44 (1), 85 (1984); J. Med. Chem., 24 (1), 5 (1981); J. Med. Chem., 25 (6), 618 (1982); J. Med. Chem., 25 (12), 1500 (1983); Steroids, 49 (6), 531 (1987); Invest. Radiol., 35 (3), 158 (2000); J. Pharm. Sci., 85 (9), 908 (1996); Pharm. Res., 13 (6), 875 (1996); J. Med. Chem., 38 (4), 636 (1995); Invest. Radiol., 29 (suppl. 2), S284 (1994); J. Med. Chem., 29 (12), 2457 (1986), International Patent Publications WO98/46275, WO95/31181, WO94/19025, U.S. Pat. Nos. 4,873,075, 4,567,034, WO96/28414, WO96/00089 and the like disclose methods of suspending or oil-emulsifying a hydrophobic iodine compound in water in the presence of a surfactant and/or oil and fat for contrast of tumor, liver, spleen, adrenal cortex, arteriosclerotic lesion, vessel pool, lymphatic system and the like. However, these methods for formulation are not sufficient in efficiency and selectivity for a purpose of selective radiography of a tissue or a lesion.

Some attempts have also been reported in which a hydrophobic iodine contrast medium or a hydrophilic contrast medium is formulated for selective accumulation in a target lesion (International Patent Publications WO95/19186, WO95/21631, WO89/00812, British Patent No. 867650, WO96/00089, WO94/19025, WO96/40615, WO95/2295, WO98/41239, WO98/23297, WO99/02193, WO97/06132, U.S. Pat. Nos. 4,192,859, 4,567,034, 4,925,649, Pharm. Res., 16 (3), 420 (1999), J. Pharm. Sci., 72 (8), 898 (1983), Invest. Radiol., 18 (3), 275 (1983)).

For example, Pharm. Res., 16 (3), 420 (1999) discloses that by injection of an oil-particle dispersion of cholesteryl iopanoate as a hydrophobic compound, the iodine compound accumulates in arteriosclerotic lesions of experimental animals. J. Pharm. Sci. 72 (8), 898 (1983) discloses examples of X-ray hepatography and splenography by injection of an oil-particle dispersion of cholesteryl iopanoate. U.S. Pat. No. 4,567,034 describes a method of selective hepatography or splenography utilizing liposomes encapsulating an ester of diatrizoic acid. International Patent Publications WO96/28414 and WO96/00089 disclose contrast media for imaging vascular pools or lymphatic systems. However, the methods using these formulations are not satisfactory in efficiency and selectivity for a purpose of selective contrast of vascular diseases, and no example thereof is reported in which vascular diseases are imaged by utilizing X-ray irradiation.

DISCLOSURE OF THE INVENTION

An object of the present invention is to provide means for highly selectively accumulating an iodine compound in a particular tissue or lesion. More specifically, the object is to provide means for selectively accumulating an iodine compound in a lesion of a vascular disease caused by abnormal proliferation of vascular smooth muscle cells such as arteriosclerosis and restenosis after PTCA. Another object of the present invention is to provide a means for imaging of a biological environment of a vascular disease or the like by X-ray radiography using the aforementioned means.

A further object of the present invention is to provide an X-ray contrast medium which enables sharp imaging of a biological environment of a tissue or a lesion in which macrophages localize such as in liver, spleen, air vesicle, lymph node, lymph vessel, renal epithelium or the like. A still further object of the present invention is to provide a contrast medium which enables identification of a site in which tumor, inflammation, or infection is progressing.

The inventors of the present invention conducted various studies to achieve the foregoing objects, and as a result, they found that liposomes containing a hydrophobic iodine compound as one of membrane components accumulated in vascular smooth muscle cells and foam macrophages, which are main components of arteriosclerotic lesion. The inventors of the present invention also found that liposomes containing a hydrophobic iodine compound, phosphatidylcholine, and phosphatidylserine as membrane components accumulated in a tissue or lesion in which macrophages localized, and that such tissue or lesion in which macrophages localized gave sharp imaging by X-ray radiography using a contrast medium comprising said liposomes. The present invention was achieve on the basis of these findings.

The present invention thus provides a liposome containing a hydrophobic iodine compound represented by the following general formula (I) as a membrane component:

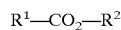

(in the formula, $R^1$ represents a substituted or unsubstituted 2,3,5-triiodophenyl group or a substituted or unsubstituted 3,4,5-triiodophenyl group; and $R^2$ represents a hydrocarbonic group having 10 or more carbon atoms).

As preferred embodiments of the present invention, provided are the aforementioned liposome, which contains a phospholipid selected from the group consisting of a phosphatidylcholine and a phosphatidylserine, preferably a combination of phosphatidylcholine and phosphatidylserine, as membrane component(s); the aforementioned liposome containing a phosphoric acid dialkyl ester, which is a diester of an alkyl containing 6 or more carbon atoms, as a membrane component; and the aforementioned liposome, wherein the hydrocarbonic group having 10 or more carbon atoms is a residue of a cholesterol derivative.

The present invention also provides an X-ray contrast medium, which comprises the aforementioned liposome. As preferred embodiments of the invention, provided are the aforementioned X-ray contrast medium, which is used for radiography of a vascular disease; and the aforementioned X-ray contrast medium, which is used for radiography of vascular smooth muscle cells which are abnormally proliferated under an influence of foam macrophages, for example, for radiography of an arteriosclerotic lesion or restenosis after PTCA.

From another aspect, the present invention provides an X-ray contrast medium for radiography of a tissue or a lesion in which macrophages localizes, which comprises a liposome containing a hydrophobic iodine compound, phosphatidylcholine, and phosphatidylserine as membrane components.

As preferred embodiments of the invention, provided are the aforementioned X-ray contrast medium, wherein the hydrophobic iodine compound is a triiodobenzene derivative having at least one substituent having 10 or more carbon atoms; the aforementioned X-ray contrast medium, wherein the liposome contains a phosphoric acid dialkyl ester, which is a diester of an alkyl containing 6 or more carbon atoms, as a membrane component; the aforementioned X-ray contrast medium, wherein the hydrocarbon group having 10 or more carbon atoms is a residue of a cholesterol derivative; the aforementioned X-ray contrast medium, wherein the tissue in which macrophages localize is selected from the group consisting of tissues of liver, spleen, air vesicle, lymph node, lymph vessel, and renal epithelium; and the aforementioned X-ray contrast medium, wherein the lesion in which macrophages localize is selected from the group consisting of tumor site, inflammation site, and infection site.

The present invention further provides a method for X-ray radiography of a tissue or a lesion in which macrophages localize, which comprises a step of performing radiography after administering an X-ray contrast medium comprising a liposome containing a hydrophobic iodine compound, phosphatidylcholine, and phosphatidylserine as membrane components to a mammal including human.

PREFERRED EMBODIMENTS OF THE INVENTION

Figure 1:
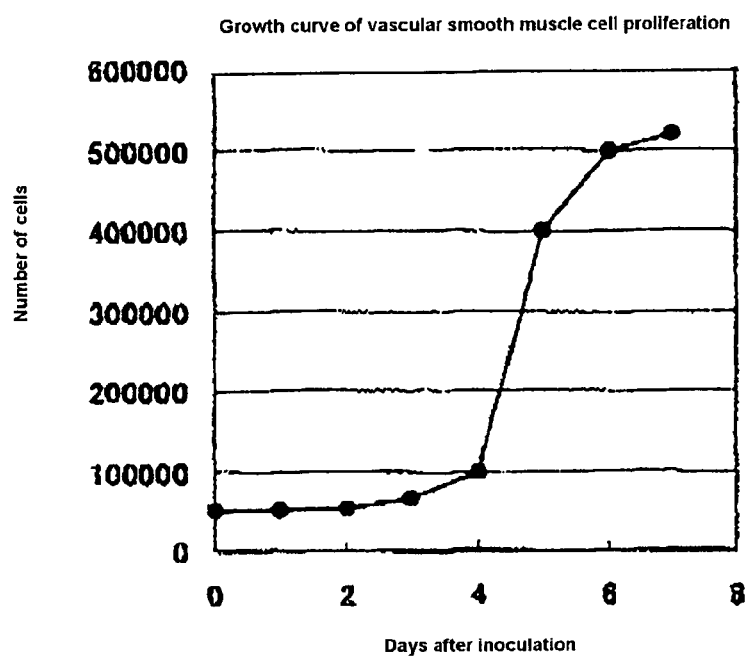
FIG. 1 shows results induction of mouse vascular smooth muscle cell proliferation in the presence of foam mouse macrophages.

The iodine compound represented by the general formula (I) is an ester compound formed from a substituted or unsubstituted 2,3,5-triiodobenzoic acid or a substituted or unsubstituted 3,4,5-triiodobenzoic acid and an alcohol having a hydrocarbonic group containing 10 or more carbon atoms. The alcohol having a hydrocarbonic group containing 10 or more carbon atoms is preferably an alcohol having a hydrophobic hydrocarbonic group for stable localization of the triiodobenzoic acid residue, as being an iodine contrasting moiety, in a bilayer of the liposome. For example, an alcohol having a hydrocarbon group containing from 18 to 40 carbon atoms is preferred (numerical ranges defined with "from-to" expression in the specification includes values of lower and upper limits). Further, the hydrocarbonic group may contain one or more hetero atoms such as an oxygen atom, nitrogen atom, or sulfur atom. The total number of oxygen atom and nitrogen atom contained in the hydrocarbon group is generally preferably 10 or less. The hetero atoms may constitute a backbone of the hydrocarbonic group and/or may be contained in a side chain.

The hydrocarbonic group more preferably has a structure similar to that of lipid components constituting biological membranes. Preferred examples of the hydrophobic iodine compounds of the general formula (I) that satisfy such requirements include, for example, ester compounds formed by the cholesterol derivatives described in J. Med. Chem., 25 (6), 618 (1982); J. Med. Chem., 24 (1), 5(1981); Appl. Radial. Isot., 37 (8), 907 (1986); Steroids, 44 (1), 85 (1984); Steroids, 14 (5), 575 (1969) and the like, and a 2,3,5-triiodobenzoic acid or 3,4,5-triiodobenzoic acid. The cholesterol derivatives described in the aforementioned references are preferred, and cholesterol is particularly preferred. Compounds in which cholesterol is bind at the 3-hydroxyl group to a 2,3,5-triiodobenzoic acid or 3,4,5-triiodobenzoic acid to form an ester bond are preferred.

In the general formula (I), the 2,3,5-triiodophenyl group or 3,4,5-triiodophenyl group may have one or more substituents on the ring. A type, substituting position, and numbers of the substituents are not particularly limited. Examples of the substituents on the ring include, for example, a substituted or unsubstituted amino group, a substituted or unsubstituted acylamino group, a hydroxyl group, a carboxyl group and the like. Preferred substituents are a substituted or unsubstituted amino group and a substituted or unsubstituted acylamino group. Examples of the amino group having a substituent include a monoalkylamino group, a dialkylamino group and so the like, and examples of the acylamino group having a substituent include trifluoroacetylamino group, p-chlorobenzoylamino group and the like.

Preferred examples of the compound represented by the general formula (I) include Compound 12 to Compound 15 among the specific compounds shown below. However, the liposomes of the present invention are not limited to those containing these compounds.

The hydrophobic iodine compound represented by the aforementioned general formula (I) is contained as a component of a membrane of the liposome, and a content of the compound in the liposome is about from 10 to 90 mass %, preferably from 10 to 80 mass %, further preferably from 20 to 80 mass %, of the total membrane components of the liposome. One kind of the hydrophobic iodine compound may be used as a membrane component, or two or more kinds of the hydrophobic iodine compounds may be used in combination.

As other components constituting the liposome membrane, any of lipid compounds ordinarily used for preparation of liposomes can be used. For example, such compounds are described in Biochim. Biophys. Acta, 150 (4), 44 (1982); Adv. in Lipid. Res., 16 (1) 1 (1978); "RESEARCH IN LIPOSOMES", P. Machy, L. Leserman, John Libbey EUROTEXT Co.); "Liposome" (Ed., Nojima, Sunamoto and Inoue, Nankodo) and the like. As the lipid compounds, phospholipids are preferred, and phosphatidylcholines (PC) are particularly preferred. Preferred examples of phosphatidylcholines include, but not limited thereto, egg PC, dimyristoyl-PC (DMPC), dipalmitoyl-PC (DPPC), distearoyl-PC (DSPC), dioleyl-PC (DOPC) and the like.

According to a preferred embodiment of the liposome of the present invention, a phospholipid selected from the group consisting of phosphatidylcholines and phosphatidylserines (PS) can be used as a membrane component of the liposome, and according to a more preferred embodiment, the both can be used in combination. Examples of the phosphatidylserines include those having lipid moieties similar to those of the phospholipids mentioned as preferred examples of the phosphatidylcholines. When a phosphatidylcholine and a phosphatidylserine are used in combination, molar ratio of PC and PS (PC:PS) used is preferably in the range of 90:10 to 10:90, further preferably 30:70 to 70:30.

Another preferred embodiment of the liposome of the present invention includes the liposome containing phosphatidylcholine and phosphatidylserine and further containing a phosphoric acid dialkyl ester as membrane components. The two alkyl groups constituting the dialkyl ester of phosphoric acid are preferably the same kind, and each group may contain 6 or more carbon atoms, preferably 10 or more carbon atoms, more preferably 12 or more carbon atoms. An upper limit of the carbon numbers of the alkyl groups is not particularly limited. The limit is generally 24 or less. Preferred examples of the phosphoric acid dialkyl ester include, but not limited thereto, dilauryl phosphate, dimyristyl phosphate, dicetyl phosphate and the like. In this embodiment, preferred amount of the phosphoric acid dialkyl ester is from 1 to 50 mass %, preferably from 1 to 30 mass %, further preferably from 1 to 20 mass % based on the total mass of phosphatidylcholine and phosphatidylserine.

In the liposome containing phosphatidylcholine, phosphatidylserine, phosphoric acid dialkyl ester, and a hydrophobic iodine compound represented by the aforementioned general formula (I) as membrane components, preferred ratio of PC, PS, phosphoric acid dialkyl ester, and hydrophobic iodine compound represented by the general formula (I) can be chosen from 5 to 40 mass %: from 5 to 40 mass %: from 1 to 10 mass %: 15-80 mass %.

The components of the liposome of the present invention are not limited to the aforementioned four kinds of compounds, and other components may be added. Examples of such components include cholesterol, cholesterol esters, sphingomyelin, monosial ganglioside GM1 derivatives described in FEBS Lett., 223, 42 (1987); Proc. Natl. Acad. Sci., USA, 85, 6949 (1988) etc., glucuronic acid derivatives described in Chem. Lett., 2145 (1989); Biochim. Biophys. Acta, 1148, 77 (1992) etc., polyethylene glycol derivatives described in Biochim. Biophys. Acta, 1029, 91 (1990); FEBS Lett., 268, 235 (1990) and the like. However, the components are not limited to these examples.

The contrast medium of the present invention provided as the first aspect is characterized to comprise the liposomes containing the compound represented by the aforementioned formula (I). The liposomes can be prepared by any methods known in the field of the art. Examples of the preparation method are described in the references as general review of liposomes mentioned above, as well as in Ann. Rev. Biophys. Bioeng., 9, 467 (1980), "Liopsomes" (Ed. by M. J. Ostro, MARCELL DEKKER, INC.) and the like. Specific examples thereof include the ultrasonication method, ethanol injection method, French press method, ether injection method, cholic acid method, calcium fusion method, freeze and thawing method, reverse phase evaporation method and the like. However, the preparation methods are not limited to these examples. Size of the liposomes may be any of those obtainable by the aforementioned methods. Generally, a size in average may be 400 nm or less, preferably 200 nm or less. Structures of the liposomes are not particularly limited, and may be unilamellar or multilamellar structure. It is also possible to formulate one or more kinds of appropriate medicaments or other contrast media in the liposomes.

The contrast medium of the present invention provided as the first aspect can be used for X-ray radiography as an iodine-containing contrast medium. The contrast medium can be preferably administered parenterally, more preferably administered intravenously. For example, preparations in the form of an injection or a drip infusion can be provided as powdery compositions in a lyophilized form, and they can be used by being dissolved or resuspended just before use in water or an appropriate solvent (e.g., physiological saline, glucose infusion, buffering solution and the like). When the liposomes of the present invention are used as an iodine-containing contrast medium, the dose can be suitably determined so that an iodine content in the liposomes becomes similar to that of a conventional iodine-containing contrast medium.

Although it is not intended to be bound by any specific theory, it is known that, in vascular diseases such as arteriosclerosis or restenosis after PTCA, vascular smooth muscle cells are abnormally proliferated and migrate into endosporium at the same time to narrow blood flow passages. Factors triggering the abnormal proliferation of normal vascular smooth muscle cells have not yet been clearly elucidated, however, it is known that migration of macrophages into endosporium and foaming are important factors. It is reported that vascular smooth muscle cells then cause phenotype conversion (from constricted to composite type).

When the liposomes of the present invention are used, the hydrophobic iodine compound represented by the general formula (I) can be selectively taken up into the vascular smooth muscle cells abnormally proliferated under influences of foam macrophages. As a result, by using the liposomes of the present invention, X-ray radiography with high contrast between a lesion and vascular smooth muscle cells in non-pathological sites. Therefore, the contrast medium of the present invention provided according to the first aspect can be suitably used particularly for radiography of vascular diseases. For example, radiography of arteriosclerotic lesion or restenosis after PTCA can be performed. Method for imaging are not particularly limited. Imaging can be performed by an ordinary method utilizing X-ray irradiation.

Further, as described in J. Biol. Chem., 265, 5226 (1990), for example, it is known that liposomes containing phospholipids, particularly liposomes formed by using PC and PS, likely to accumulate on macrophages with the aid of scavenger receptors. Therefore, by using the liposomes of the present invention, the hydrophobic iodine compound represented by the general formula (I) can be accumulated in a tissue or a lesion in which macrophages localize. When the liposomes of the present invention are used, it is possible to accumulate a larger amount of the iodine compound in macrophages as compared with a contrast medium utilizing a suspension or an oil emulsion as an conventional technique.

Examples of tissues in which localization of macrophages is observed, which can be suitably radiographed by the method of the present invention, include blood vessel, liver, spleen, air vesicle, lymph node, lymph vessel, and renal epithelium. Further, it is known that macrophages accumulate in lesions in certain classes of diseases. Examples of such diseases include tumor, arteriosclerosis, inflammation, infection and the like. Therefore, lesions of such diseases can be identified by using the liposomes of the present invention. In particular, it is known that foam macrophages, which take up a large amount of denatured LDL with the aid of scavenger receptors, accumulate in atherosclerosis lesions at an early stage (Am. J. Pathol., 103, 181 (1981); Annu. Rev. Biochem., 52, 223 (1983)). Therefore, by performing radiography after accumulation of the liposomes of the present invention in the macrophages, it is possible to identify locations of atherosclerosis lesions at an early stage, which is hardly achievable by other means.

The second contrast medium of the present invention provided according to the second aspect is an X-ray contrast medium for radiography of a tissue or a lesion in which macrophages localize, which is characterized to comprise liposomes containing a hydrophobic iodine compound, phosphatidylcholine, and phosphatidylserine as membrane components.

Type of the hydrophobic iodine compounds are not particularly limited. For example, iodobenzene derivatives are preferred, and triiodobenzene derivatives having at least one substituent containing 10 or more carbon atoms are more preferred. Substituting positions of three iodine atoms of the triiodobenzene derivatives are not particularly limited. Preferred examples of the triiodobenzene derivatives include 1,3,5-triiodobenzene derivatives, 1,2,4-triiodobenzene derivatives, 1,2,3-triiodobenzene derivatives and the like. Further, the hydrophobic iodine compounds represented by the aforementioned formula (I) are also preferred.

The substituent containing 10 or more carbon atoms is preferably a hydrophobic group for stable localization of the triiodobenzene residue which is a contrasting moiety. For example, substituents containing 18 or more carbon atoms, in which a total number of oxygen atom and nitrogen atom is 10 or less, are more preferred. An upper limit of the carbon number of the substituents containing 10 or more carbon atoms is not particularly limited. Generally, the limit is 40 or less. The hydrophobic substituent more preferably has a structure similar to that of biological membrane constituting lipid components. Preferred examples of the hydrophobic iodine compounds that satisfy such requirements include, for example, 1,3,5-triiodobenzene derivatives having as a substituent a residue of any of the cholesterol derivatives disclosed in J. Med. Chem., 25 (12), 1500 (1982); Steroids, 49 (6), 531 (1987); Pharm. Res., 6 (12), 1011 (1989); International Patent Publications WO95/19186, WO 96/28414 and the like.

Other preferred examples of the hydrophobic iodine compound include, for example, 1,2,4- or 1,2,3-triiodobenzene derivatives having, as a substituent, a residue of any of cholesterol derivatives described in J. Med. Chem., 25 (6), 618 (1982); J. Med. Chem., 24 (1), 5(1981); Appl. Radial. Isot., 37 (8), 907 (1986); Steroids, 44 (1), 85 (1984); Steroids, 14 (5), 575 (1969) and the like.

The cholesterol derivatives described in the aforementioned references are preferred, and particularly preferred is cholesterol. Compounds are preferred in which cholesterol is bound at the 3-hydroxyl group to the hydrophobic iodine compound, for example, to a triiodophenyl group. As means for binding the hydroxyl group of cholesterol to the hydrophobic iodine compound such as a triiodophenyl group, an ester bond, ether bond, urethane bond, carbonate bond and so forth can be used. An ester bond is preferred. Cholesterol and the hydrophobic iodine compound such as a triiodophenyl group may be directly bound via any of the bonds mentioned above or bound by means of an appropriate bridging group. Examples of the appropriate bridging group include a linear or branched alkylene groups having 5 or less carbon atoms.

The hydrophobic iodine compound, preferably a triiodobenzene compound, may have one or more substituents other than the aforementioned substituent having 10 or more carbon atoms. The type, substituting position, and number of the substituents are not particularly limited. For example, a substituted or unsubstituted amino group, a substituted or unsubstituted acylamino group, a hydroxyl group, a carboxyl group and the like may substitute on a benzene ring of the hydrophobic iodine compound. Preferred substituents are a substituted or unsubstituted amino group and a substituted or unsubstituted acylamino group. Examples of the amino group having a substituent include a monoalkylamino group, a dialkylamino group and the like, and examples of the acylamino group having a substituent include trifluoroacetylamino group, p-chlorobenzoylamino group and the like.
Preferred examples of the hydrophobic iodine compound are listed below. However, the liposome of the present invention is not limited to those containing these compounds.
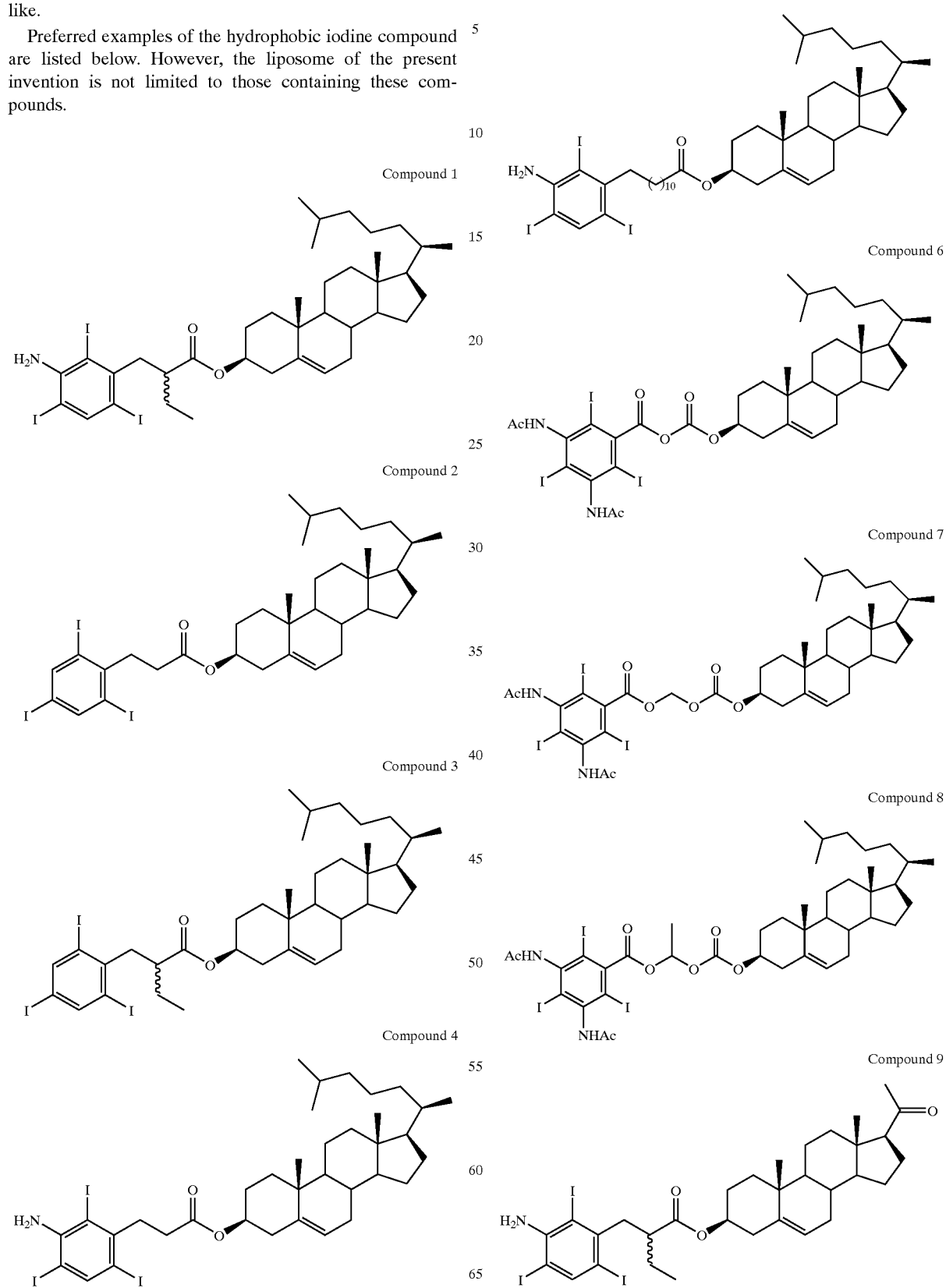

-continued

Compound 10

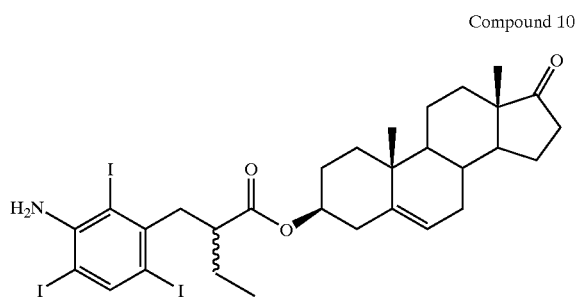

Compound 11

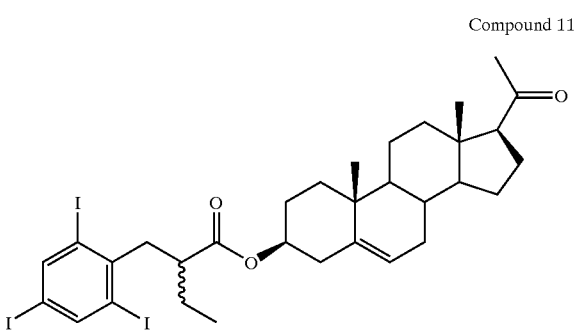

Compound 12

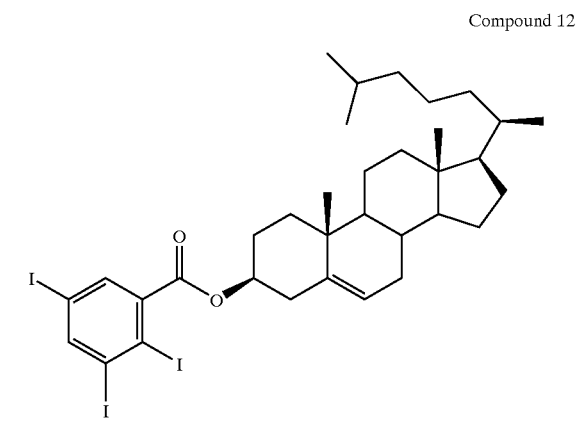

Compound 13

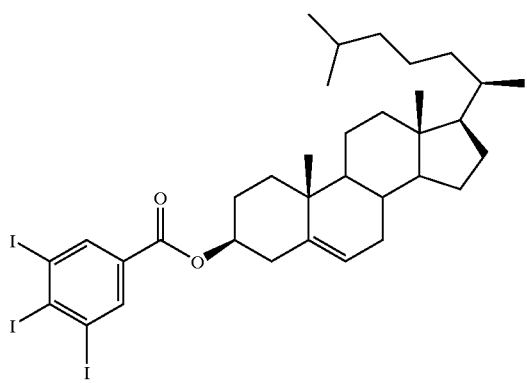

-continued

Compound 14

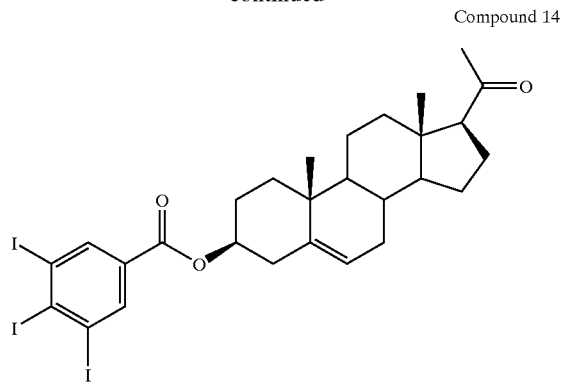

Compound 15

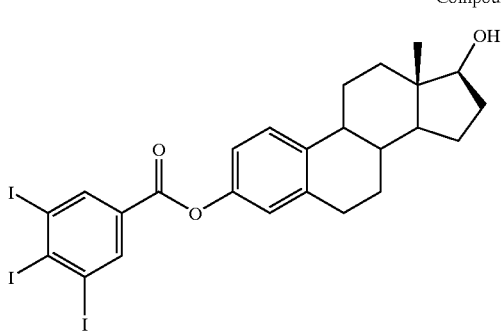

The hydrophobic iodine compound is contained as a membrane component of the liposome, and content of the compound in the liposome is about from 10 to 90 mass %, preferably from 10 to 80 mass %, further preferably from 20 to 80 mass %, of the total membrane components of the liposome. One kind of the hydrophobic iodine compound may be used as a membrane component, or two or more kinds of the hydrophobic iodine compounds may be used in combination.

The liposome contained in the contrast medium of the present invention provided according to the second aspect is characterized to contain the hydrophobic iodine compound, phosphatidylcholine (PC), and phosphatidylserine (PS) in combination as membrane components. Preferred examples of phosphatidylcholines include, but not limited thereto, egg PC, dimyristoyl-PC (DMPC), dipalmitoyl-PC (DPPC), distearoyl-PC (DSPC), dioleyl-PC (DOPC) and the like. Preferred examples of the phosphatidylserines include those having lipid moieties similar to those of the phospholipids mentioned as preferred examples of the phosphatidylcholines. Preferred molar ratio of PC and PS used is in the range of from 90:10 to 10:90, more preferably from 30:70 to 70:30.

An example of another preferred embodiment of the liposome, which is contained in the contrast medium of the present invention provided according to the second aspect, include the liposome containing the hydrophobic iodine compound, phosphatidylcholine, and phosphatidylserine, and further containing a phosphoric acid dialkyl ester as membrane components. The two alkyl groups that constitute the dialkyl ester of phosphoric acid are preferably the same, and each may contain 6 or more carbon atoms, preferably 10 or more carbon atoms, more preferably 12 or more carbon atoms. An upper limit of the carbon numbers of the alkyl groups is not particularly limited. Generally the limit is 24 or less. Preferred examples of the phosphoric acid dialkyl ester include, but not limited thereto, dilauryl phosphate, dimyristyl phosphate, dicetyl phosphate and the like. According to this particular embodiment, preferred amount of the phosphoric acid dialkyl ester is from 1 to 50 mass %, preferably 1 to 30 mass %, further preferably 1 to 20 mass % based on total mass of phosphatidylcholine and phosphatidylserine.

In the liposome containing phosphatidylcholine, phosphatidylserine, phosphoric acid dialkyl ester, and the hydrophobic iodine compound as membrane components, preferred mass ratio of PC, PS, phosphoric acid dialkyl ester and the hydrophobic iodine compound can be chosen from 5 to 40 mass %:from 5 to 40 mass %; from 1 to 10 mass %:from 15 to 80 mass %.

The components of the liposome of the present invention provided according to the second aspect are not limited to the aforementioned four kinds of compounds, and other components may be added. Examples of such components include cholesterol, cholesterol esters, sphingomyelin, monosial ganglioside GM1 derivatives described in FEBS Lett., 223, 42 (1987); Proc. Natl. Acad. Sci., USA, 85, 6949 (1988) etc., glucuronic acid derivatives described in Chem. Lett., 2145 (1989); Biochim. Biophys. Acta, 1148, 77 (1992) etc., polyethylene glycol derivative described in Biochim. Biophys. Acta, 1029, 91 (1990); FEBS Lett., 268, 235 (1990) and the like. However, the components are not limited to these examples.

The liposome contained in the contrast medium of the present invention provided according to the second aspect can be prepared by any methods known in the filed of the art. Examples of the preparation method are described in the above-mentioned references as general reviews of liposomes, as well as Ann. Rev. Biophys. Bioeng., 9, 467 (1980), "Liopsomes" (Ed. by M. J. Ostro, MARCELL DEKKER, INC.) and the like. Specific examples include the ultrasonication method, ethanol injection method, French press method, ether injection method, cholic acid method, calcium fusion method, freeze and thawing method, reverse phase evaporation method and the like. However, the preparation method is not limited to these examples. A size of the liposomes may be any of sizes obtainable by the aforementioned methods. The size in average is usually 400 nm or less, preferably 200 nm or less. Structures of the liposomes are not particularly limited, and they may have a unilamellar or multilamellar structure. It is also possible to formulate one or more kinds of appropriate medicaments or other contrast media in the liposomes.

The contrast medium of the present invention provided according to the second aspect can be used for X-ray radiography as an iodine-containing contrast medium. This contrast medium can be preferably administered parenterally, more preferably administered intravenously. For example, preparations in a form of an injection or a drip infusion can be provided as powdery compositions in a lyophilized form, and they can be used by being dissolved or resuspended just before use in water or an appropriate solvent (e.g., physiological saline, glucose infusion, buffer and the like). When the liposomes of the present invention are used as an iodine-containing contrast medium, a dose can be suitably determined so that an iodine content in the liposomes is similar to that of a conventional iodine-containing contrast medium.

As described in J. Biol. Chem., 265, 5226 (1990), for example, it is known that liposomes containing phospholipids, particularly liposomes formed by using PC and PS, likely to accumulate in macrophages with the aid of scavenger receptors. Therefore, by using the liposomes of the present invention provided according to the second aspect, the hydrophobic iodine compound can be accumulated in a tissue or a lesion in which macrophages localize. As described in the examples of the present specification, a method utilizing the contrast medium of the present invention can achieve a larger amount of accumulation of the iodine compound in macrophages compared with a method utilizing a suspension or an oil emulsion as a conventional technique.

Examples of tissue in which macrophages localize, which can be suitably radiographed by using the contrast medium of the present invention, include liver, air vesicle, lymph node, lymph vessel, and renal epithelium. Further, it is known that macrophages accumulate in lesions of certain class of diseases. Examples of such diseases include tumor, inflammation, infection and the like. Therefore, lesions of such diseases can be identified by using the liposomes of the present invention provided according to the second aspect.

EXAMPLES

The present invention will be explained more specifically with reference to the examples. However, the scope of the present invention is not limited to the following examples. The compound numbers used in the examples correspond to the numbers of the compounds mentioned above as preferred compounds.

Example 1

Preparation of Culture System of Vascular Smooth Muscle Cells of which Proliferation is Activated by Foam Macrophages Vascular smooth muscle cells were isolated from mouse aorta endothelium ("Tissue Culture Method", 10th Edition, ed. by the Japanese Tissue Culture Association, published by Kodansha, 1998). The isolated vascular smooth muscle cells were suspended in 10% FBS Eagle's MEM (GIBCO, No. 11095-080) and inoculated in wells of a 12-well microplate (FALCON, No. 3503). The number of the cells in each well was adjusted to 10,000 cells. The cells were cultured for 3 days under conditions of 37° C. and 5% $CO_2$.

Figure 2:
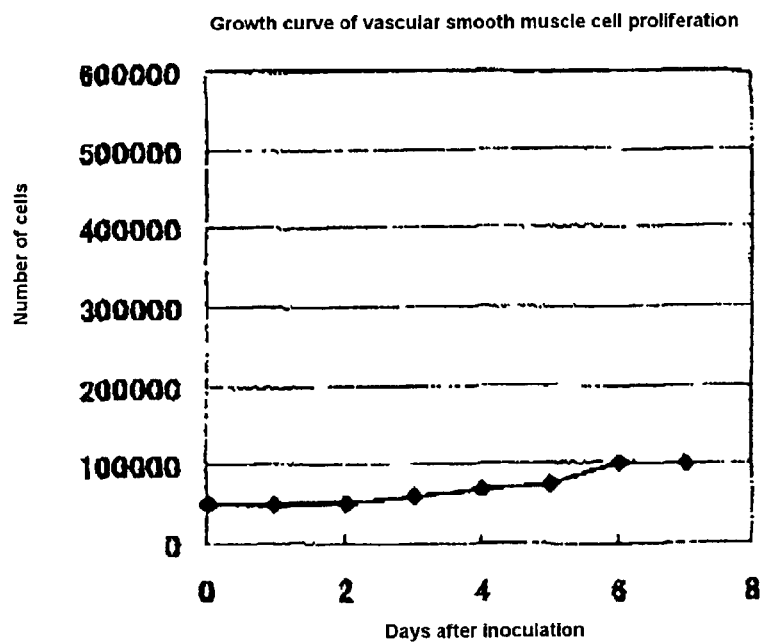
FIG. 2 shows a proliferation curve of mouse vascular smooth muscle cells obtained without addition of foam mouse macrophages.

Then, foamed mouse peritoneal macrophages were prepared according to the method described in Biochimica Biophysica Acta, 1213, 127 (1994). 200,000 cells of the foam macrophages were separated and inoculated on an insert cell (FALCON, No. 3180) placed on each well of the microplate where the vascular smooth muscle cells were cultured on the bottom surface. The cells were cultured for 5 days under conditions of 37° C. and 5% $CO_2$. The cell numbers of the vascular smooth muscle cells in the above experiment are shown in FIG. 1. Although the vascular smooth muscle cells gently proliferated at an early stage after the start of the culture, they actively proliferated after the addition of the foam macrophages on the 3rd day and a subsequent induction period of about 1 day. A proliferation curve of vascular smooth muscle cells not added with the macrophages is shown in FIG. 2. Comparison of the results shown in FIGS. 1 and 2 clearly indicates activating effect of the foam macrophages on the proliferation.

Example 2

Verification of Expression of Scavenger Receptors on Vascular Smooth Muscle Cells It is known that vascular smooth muscle cells in an arteriosclerotic lesion express scavenger receptors on their surfaces to take up oxidized LDL (Biochem. Phamacol., 15:57 (4), 383 (1999); Exp. Mol. Pathol., 64 (3), 127–45, 1997). The vascular smooth muscle cells of the culture system of FIG. 1 were immunostained by using mouse scavenger receptor antibodies. As a result, although the expression was not observed on the vascular smooth muscle cells on the 3rd day from the inoculation, clear staining was observed on the 6th day from the inoculation. When the foam macrophages on the cell filter was also similarly immunostained, clear staining was also observed.

Example 3

Uptake of Oxidized LDL by Vascular Smooth Muscle Cells

In the culture system of FIG. 1, $^{125}$I-labeled oxidized LDL was added to the medium for the vascular smooth muscle cells on the 3rd day and 6th day from the inoculation. $^{125}$I taken up into the cells was counted 24 hours after each addition. The results are shown in Table 1. Clear difference in uptake amount was observed between the results on the 3rd day and 6th day.

TABLE 1

| Days | Uptake of $^{125}$I-oxLDL (× 1,000 cpm) |
|---|---|
| 3 Days after inoculation | 0.52 ± 0.11 |
| 6 Days after inoculation | 2.2 ± 0.4 |

The above results indicate that the vascular smooth muscle cells cultured in the aforementioned cell culture system had properties similar to those of smooth muscle cells in a lesion of arteriosclerosis, restenosis or the like. Because the vascular smooth muscle cells cultured in the culture system in FIG. 1 had properties of healthy blood vessel until the 3rd day from the inoculation and properties of smooth muscle cells in an arteriosclerotic lesion on and after the 7th day from the inoculation, a screening of a medicament selective to the lesion can be performed by comparing actions of the medicament on each of the above cells. In particular, the system can be utilized for searching of a drug delivery system selective to a lesion, searching of a medicament that is selectively toxic for cells in a lesion, searching of a medicament that selectively terminates cell cycle of cells in a lesion and the like.

Example 4

Preparation of Liposomes

Egg PC (Funakoshi, No. 1201-41-0214), egg PS (Funakoshi, No.1201-42-0226), dicetyl phosphate (DCP, Funakoshi, No.1354-14-8165) and Compound 12 as a hydrophobic iodine compound synthesized by the method described in J. Med. Chem., 24 (1) 5 (1981), in the ratios described blow, were dissolved in methylene chloride contained in an eggplant-shaped flask to form a uniform solution, and then the solvent was evaporated under reduced pressure to form a thin membrane on the bottom of the flask. The thin membrane was dried in vacuo, then added with 1.5 ml of 0.9% physiological saline (Hikari Pharmaceutical, No.512) and ultrasonicated (probe type oscillator, Branson, No.3542, 0.1 mW) for 5 minute with ice cooling to obtain a uniform liposome dispersion. Size of the particles contained in the resulting dispersion was measured by using WBC analyzer (Nihon Kohden, A-1042). The particle size was 40 to 65 nm.

TABLE 2

| Liposome | PC | PS | Compound 12 |
|---|---|---|---|
| Preparation 1 | 50 nmol | 50 nmol | 40 nmol |
| Preparation 2 | 50 nmol | 50 nmol | 75 nmol |
| Preparation 3 | 50 nmol | 50 nmol | 150 nmol |

Example 5

Selective Uptake of Liposome Preparations by Vascular Smooth Muscle Cells

The three types of liposomes prepared in Example 4 were added to the smooth muscle cell culture system of FIG. 1 or 2 in Example 1 according to the following protocols (1), (2) and (3), and then the culture was continued.

(1) A liposome preparation was added on the 3rd day to the culture system of FIG. 2 not added with the foam macrophages and culture was continued for 1 day.

(2) A liposome preparation was added on the 5th day to the culture system of FIG. 1 added with the foam macrophages and culture was continued for 1 day.

(3) A liposome preparation was added on the 7th day to the culture system of FIG. 1 added with the foam macrophages and culture was continued for 1 day.

Figure 3:
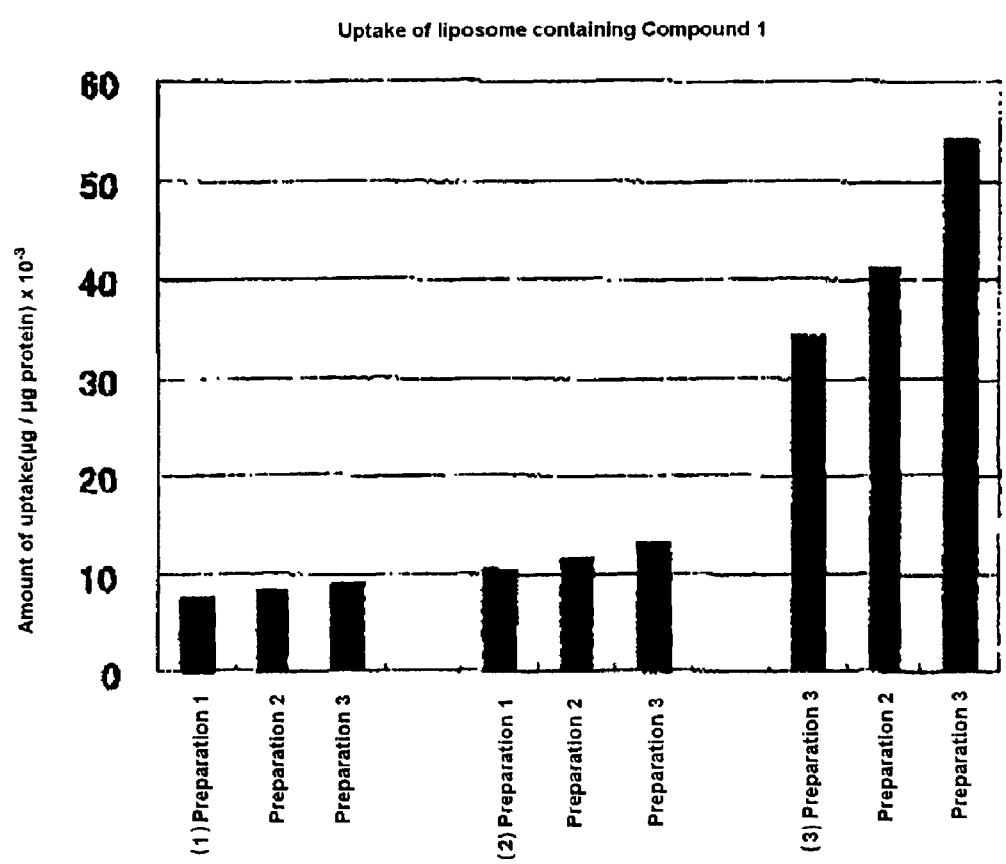
FIG. 3 shows uptake of liposomes by mouse vascular smooth muscle cells. In the figure, (1) shows results obtained by adding a liposome preparation on the 3rd day to the culture system of FIG. 2 without addition of foam macrophages, and then continuing the culture for 1 day, (2) shows results obtained by adding a liposome preparation on the 5th day to the culture system of FIG. 1, which was added with foam macrophages, and then continuing culture for 1 day, and (3) shows results obtained by adding a liposome preparation on the 7th day to the culture system of FIG. 1, which was added with foam macrophages, and then continuing culture for 1 day (3).

After addition of liposomes and post-culture according to each of protocols (1) to (3) were completed, the supernatant was removed and the residue was washed three times with Hank's buffer (Nissui Pharmaceutical, Code 05906, pH 7.2), added with 1.5% SDS solution (Wako Pure Chemical Industries, 199-07141) and incubated at 37° C. for 30 minutes to lyse the cells, and amount of Compound 12 taken up into the cells was measured by HPLC. The results are shown in FIG. 3. Clear differences in the amounts of the hydrophobic iodine compound taken up into the vascular smooth muscle cells by means of the liposomes of the present invention were observed before and after the proliferation was initiated under influence of the foam macrophages.

Example 6

Comparative Example

Figure 4:
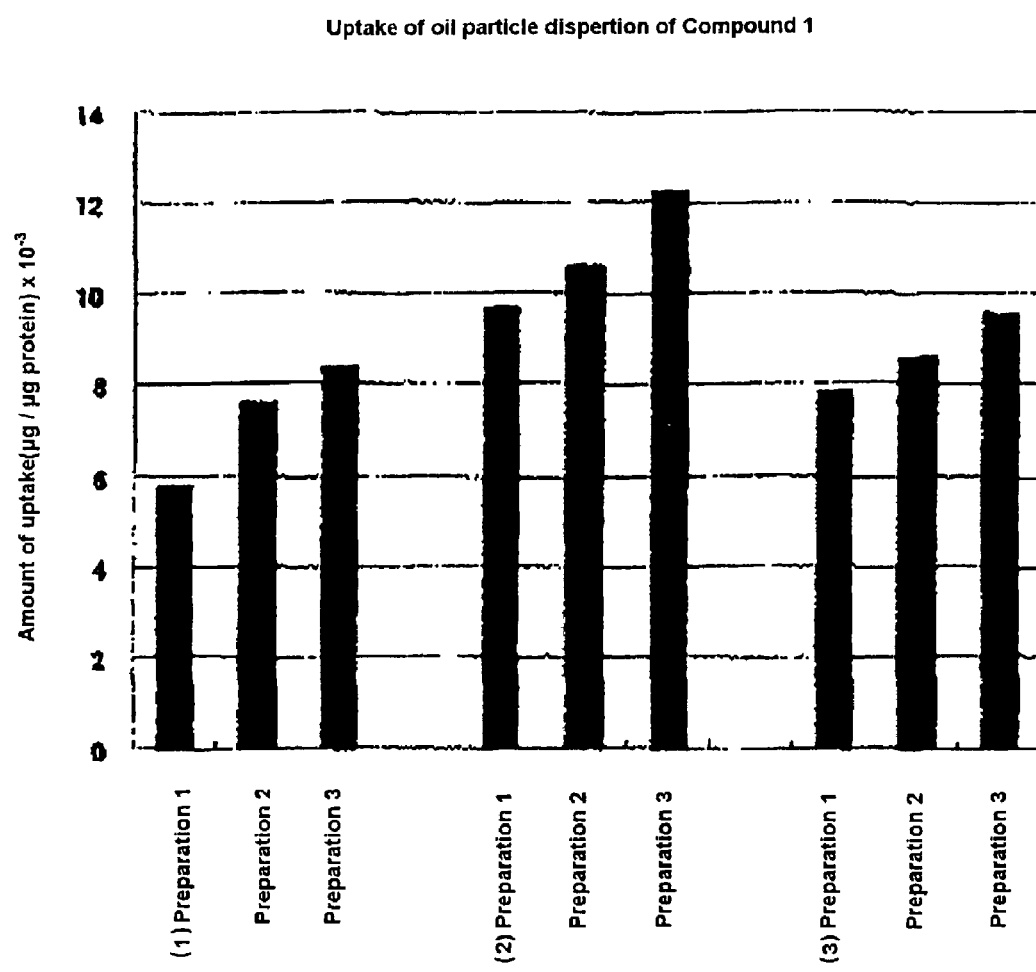
FIG. 4 shows the results obtained by using an oil particle dispersion instead of the liposomes of the present invention.

An oil particle suspension of Compound 12 was prepared according to the method described in Pharm. Res., 6, (12) 1011 (1989). The suspension was added to the cell culture system under the same conditions as those used in Example 5 (Protocols (1), (2) and (3)) in such an amount that the amount of Compound 12 became the same as those of Example 5, and amounts of Compound 12 taken up into the vascular smooth muscle cells were measured by HPLC. The results are shown in FIG. 4. From comparison of the results shown in FIGS. 3 and 4, it is clear that, by using the liposomes of the present invention, the iodine-containing contrast medium can be more efficiently and more selectively accumulated in the vascular smooth muscle cells abnormally proliferating under influence of foam macrophages compared to the known oil particle suspension.

Example 7

Preparation of Liposomes

Uniform liposome dispersions were obtained in the same manner as that of Example 4. Sizes of the particles contained in the resulting dispersions were measured by using WBC analyzer (Nihon Kohden, A-1042). The particle sizes were 40 to 65 nm.

TABLE 3

| Liposome | PC | PS | DCP | Compound 1 |
|---|---|---|---|---|
| Preparation 4 | 50 nmol | 50 nmol | 10 nmol | 40 nmol |
| Preparation 5 | 50 nmol | 50 nmol | 10 nmol | 75 nmol |
| Preparation 6 | 50 nmol | 50 nmol | 10 nmol | 150 nmol |

Example 8

Selective Uptake of Liposome Preparation by Macrophages

Foamed mouse peritoneal macrophages were prepared according to the method described in Biochimica Biophysica Acta, 1213, 127–134 (1994). 200,000 cells of the foam macrophages were separated, suspended in 10% FBS Eagle's MEM (GIBCO, No. 11095-080), inoculated in each well of a 12-well microplate (FALCON, No.3503) and cultured for 5 days under conditions of 37° C. and 5% $CO_2$. Then, each of Preparations 1 to 3 obtained in Example 4 and Preparations 4 to 6 obtained in Example 7 was added to the wells, and culture was further continued for 1 day. Then, the supernatant was removed and the residue was washed three times with Hank's buffer (Nissui Pharmaceutical, Code 05906, pH 7.2), added with 1.5% SDS solution (Wako Pure Chemical Industries, 199-07141) and incubated at 37° C. for 30 minutes to lyse the cells. Amounts of Compound 1 or Compound 12 intracellularly taken up were measured by HPLC. The results are shown in Table 4.

TABLE 4

Uptake of liposome preparation by macrophages

|  | Amount of taken-up iodine compound |
|---|---|
| Preparation 1 (Compound 12) | 19 |
| Preparation 2 (Compound 12) | 21 |
| Preparation 3 (Compound 12) | 24 |
| Preparation 4 (Compound 1) | 35 |
| Preparation 5 (Compound 1) | 34 |
| Preparation 6 (Compound 1) | 38 |

Unit: (nmol/µg of protein) × $10^{-3}$

Example 9

Comparative Example

Oil particle suspensions of Compound 1 or Compound 12 were prepared according to the method described in Pharm. Res., 6, (12) 1011 (1989). Each of the suspensions was added to the cell culture system under the same conditions as those used in Example 8 in such an amount that the amount of Compound 1 or Compound 12 was same as each of those used in Example 8, and amounts of Compound 1 or Compound 12 taken up into the macrophages were measured by HPLC. The results are shown in FIG. 5. From comparison of the results shown in FIGS. 4 and 5, it is clear that, by using the contrast medium containing liposomes of the present invention, the iodine compounds can be more efficiently and more selectively accumulated in macrophages compared to the known oil particle suspension.

TABLE 5

|  | Amount of taken-up iodine compound |
|---|---|
| Added in the same amount as Preparation 1 (Compound 12) | 1.5 |
| Added in the same amount as Preparation 2 (Compound 12) | 2.3 |
| Added in the same amount as Preparation 3 (Compound 12) | 1.9 |
| Added in the same amount as Preparation 4 (Compound 1) | 4.8 |
| Added in the same amount as Preparation 5 (Compound 1) | 5.3 |
| Added in the same amount as Preparation 6 (Compound 1) | 5.9 |

Unit: (nmol/µg of protein) × $10^{-3}$

The liposomes of the present invention can achieve accumulation of the hydrophobic iodine compounds represented by the general formula (I) in vascular smooth muscle cells abnormally proliferating under influence of foam macrophages, and are useful as an X-ray contrast medium for radiography of a lesion of a vascular disease caused by abnormal proliferation of vascular smooth muscle cells. Further, the contrast medium of the present invention provided according to the second aspect can achieve accumulation of iodine compounds in macrophages, and is useful as an X-ray contrast medium for radiography of a tissue or a lesion in which macrophages localize.

What is claimed is:

1. A liposome containing a hydrophobic iodine compound represented by the following general formula (I) as a membrane component:

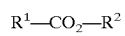

wherein $R^1$ represents a substituted or unsubstituted 2,3,5-triiodophenyl group or a substituted or unsubstituted 3,4,5-triiodophenyl group; and $R^2$ represents a hydrocarbon group having 10 or more carbon atoms, wherein said hydrocarbon group is a residue of a cholesterol derivative.

2. The liposome according to claim 1, which contains a combination of phosphatidylcholine and phosphatidylserine as membrane components.

3. The liposome according to claim 1 or 2, which contains a phosphoric acid dialkyl ester as being a diester of an alkyl containing 6 or more carbon atoms as a membrane component.

4. An X-ray contrast medium, which comprises a liposome according to claim 1.

5. The X-ray contrast medium according to claim 4, which is used for radiography of a vascular disease.

6. The X-ray contrast medium according to claim 4, which is used for radiography of vascular smooth muscle cells abnormally proliferated under an influence of foam macrophages.

7. An X-ray contrast medium for radiography of a tissue or a lesion in which macrophages localize, which comprises a liposome containing a hydrophobic iodine compound, phosphatidylcholine, and phosphatidylserine as membrane components, wherein said hydrophobic iodine compound has as a substituent a hydrocarbon group having 10 or more carbon atoms and which is a residue of a cholesterol derivative.

8. The X-ray contrast medium according to claim 7, wherein the hydrophobic iodine compound is a triiodobenzene derivative having at least one substituent having 10 or more carbon atoms.

9. The X-ray contrast medium according to claim 7 or 8, wherein the liposome contains a phosphoric acid dialkyl ester as being a diester of an alkyl containing 6 or more carbon atoms as a membrane component.

10. The X-ray contrast medium according to claim 7, wherein the tissue in which macrophages localize is selected from the group consisting of tissues of liver, spleen, air vesicle, lymph node, lymph vessel, and renal epithelium.

11. The X-ray contrast medium according to claim 7, wherein the lesion in which macrophages localize is selected from the group consisting of tumor site, inflammation site, and infection site.

* * * * *